US012685651B2

(12) United States Patent
Otto et al.

(10) Patent No.:  US 12,685,651 B2
(45) Date of Patent:       Jul. 21, 2026

(54) SYSTEM AND METHOD FOR LIGAMENT BALANCING USING ROBOTICALLY HELD DEVICE

(71) Applicant: MAKO Surgical Corp., Weston, FL (US)

(72) Inventors: Jason Otto, Plantation, FL (US); Xiao Hui Gao, Weston, FL (US)

(73) Assignee: MAKO SURGICAL CORP., Weston, FL (US)

( * ) Notice: Subject to any disclaimer, the term of this patent is extended or adjusted under 35 U.S.C. 154(b) by 59 days.

(21) Appl. No.: 18/802,627

(22) Filed: Aug. 13, 2024

(65) Prior Publication Data

US 2024/0398585 A1       Dec. 5, 2024

Related U.S. Application Data

(63) Continuation of application No. 17/257,186, filed as application No. PCT/US2020/051743 on Sep. 21, 2020, now Pat. No. 12,064,358.

(60) Provisional application No. 62/905,037, filed on Sep. 24, 2019.

(51) Int. Cl.
*A61F 2/46*              (2006.01)

(52) U.S. Cl.
CPC ............ *A61F 2/4657* (2013.01); *A61F 2/461* (2013.01); *A61F 2002/4632* (2013.01); *A61F 2002/4666* (2013.01)

(58) Field of Classification Search
CPC .................... A61F 2/4657; A61F 2/461; A61F 2002/4666; A61F 2002/4632
See application file for complete search history.

(56) References Cited

U.S. PATENT DOCUMENTS

| | | | |
|---|---|---|---|
| 4,995,875 | A | 2/1991 | Coes |
| 5,470,354 | A | 11/1995 | Hershberger et al. |
| 5,860,980 | A | 1/1999 | Axelson et al. |
| 6,558,392 | B1 | 5/2003 | Martini |
| 6,859,661 | B2 | 2/2005 | Tuke |
| 7,412,897 | B2 | 8/2008 | Crottet et al. |

(Continued)

FOREIGN PATENT DOCUMENTS

| | | | |
|---|---|---|---|
| DE | 20 2010 000 341 U1 | 5/2010 | |
| EP | 2 011 442 A1 | 1/2009 | |

(Continued)

OTHER PUBLICATIONS

U.S. Appl. No. 62/817,355, filed Mar. 12, 2019, MAKO Surgical Corp.

(Continued)

*Primary Examiner* — Andrew Yang
(74) *Attorney, Agent, or Firm* — Foley & Lardner LLP

(57)       ABSTRACT

A method of assessing ligament balance in a joint. The method comprising forcing, by motors of joints of an articulated arm of a robotic device, a ligament balancing device to apply a first force to a first bone of the joint in contact with the ligament balancing device, holding the first bone with the first force while allowing manual manipulation of a second bone of the joint and collecting a force measurement, and determining, by a processor in communication with the robotic device, a force applied to one or more ligaments of the joint based on the force measurement.

20 Claims, 8 Drawing Sheets

(56)        References Cited

U.S. PATENT DOCUMENTS

| | | | |
|---|---|---|---|
| 7,442,196 | B2 | 10/2008 | Fisher et al. |
| 7,615,055 | B2 | 11/2009 | Disilvestro |
| 7,837,691 | B2 | 11/2010 | Cordes et al. |
| 8,010,180 | B2 | 8/2011 | Quaid et al. |
| 8,118,815 | B2 | 2/2012 | Van Der Walt |
| 8,197,489 | B2 | 6/2012 | Chessar et al. |
| 8,211,041 | B2 | 7/2012 | Fisher et al. |
| 8,323,290 | B2 | 12/2012 | Metzger et al. |
| 8,337,508 | B2 | 12/2012 | Lavallee et al. |
| 8,394,104 | B2 | 3/2013 | Disilvestro |
| 8,491,589 | B2 | 7/2013 | Fisher et al. |
| 8,506,571 | B2 | 8/2013 | Chana et al. |
| 8,516,907 | B2 | 8/2013 | Stein et al. |
| 8,998,910 | B2 | 4/2015 | Borja et al. |
| 9,351,850 | B2 | 5/2016 | Fischer et al. |
| 9,439,656 | B2 | 9/2016 | Chana et al. |
| 9,538,953 | B2 | 1/2017 | Sherman et al. |
| 9,539,116 | B2 | 1/2017 | Claypool et al. |
| 9,554,745 | B2 | 1/2017 | Nguyen et al. |
| 9,572,588 | B2 | 2/2017 | Fisher et al. |
| 9,642,571 | B2 | 5/2017 | Mcintosh et al. |
| 9,665,686 | B2 | 5/2017 | Van Vorhis et al. |
| 10,198,968 | B2 | 2/2019 | Imhauser et al. |
| 10,285,683 | B2 * | 5/2019 | Plaskos .................. A61B 34/10 |
| 11,051,798 | B2 | 7/2021 | Plaskos et al. |
| 2005/0038442 | A1 | 2/2005 | Freeman |
| 2007/0055176 | A1 | 3/2007 | Branch et al. |
| 2007/0066917 | A1 | 3/2007 | Hodorek et al. |
| 2007/0179626 | A1 | 8/2007 | De La Barrera et al. |
| 2007/0219561 | A1 | 9/2007 | Lavallee et al. |
| 2007/0244488 | A1 | 10/2007 | Metzger et al. |
| 2008/0262812 | A1 | 10/2008 | Arata et al. |
| 2009/0018544 | A1 | 1/2009 | Heavener |
| 2010/0198275 | A1 | 8/2010 | Chana et al. |
| 2010/0217156 | A1 | 8/2010 | Fisher et al. |
| 2010/0249658 | A1 | 9/2010 | Sherman et al. |
| 2010/0249659 | A1 | 9/2010 | Sherman et al. |
| 2010/0250571 | A1 | 9/2010 | Pierce et al. |
| 2010/0326210 | A1 | 12/2010 | Stein et al. |
| 2010/0331737 | A1 | 12/2010 | Stein et al. |
| 2011/0319755 | A1 | 12/2011 | Stein et al. |
| 2012/0172762 | A1 | 7/2012 | Boyer et al. |
| 2012/0232429 | A1 | 9/2012 | Fischer et al. |
| 2012/0330368 | A1 | 12/2012 | Dunn |
| 2013/0023795 | A1 | 1/2013 | Stein et al. |
| 2013/0079669 | A1 | 3/2013 | Stein et al. |
| 2013/0079670 | A1 | 3/2013 | Stein et al. |
| 2013/0079674 | A1 | 3/2013 | Stein et al. |
| 2013/0079675 | A1 | 3/2013 | Stein et al. |
| 2013/0079884 | A1 | 3/2013 | Stein et al. |
| 2013/0102929 | A1 | 4/2013 | Haight et al. |
| 2013/0103038 | A1 | 4/2013 | Fischer et al. |
| 2013/0226036 | A1 | 8/2013 | Stein et al. |
| 2014/0081181 | A1 | 3/2014 | Branch et al. |
| 2014/0188129 | A1 | 7/2014 | Kang |
| 2015/0342588 | A1 | 12/2015 | Bechtold et al. |
| 2016/0278754 | A1 | 9/2016 | Todorov et al. |
| 2016/0346044 | A1 | 12/2016 | Brown et al. |
| 2017/0156736 | A1 | 6/2017 | Claypool et al. |
| 2017/0245872 | A1 | 8/2017 | Rock et al. |
| 2017/0360512 | A1 | 12/2017 | Couture et al. |
| 2018/0049895 | A1 | 2/2018 | Haight et al. |
| 2018/0085134 | A1 | 3/2018 | Uthgenannt |
| 2018/0098774 | A1 | 4/2018 | Bonutti |
| 2018/0132949 | A1 | 5/2018 | Merette et al. |
| 2018/0221008 | A1 | 8/2018 | Todorov et al. |
| 2018/0360478 | A1 | 12/2018 | Toler |
| 2019/0183411 | A1 | 6/2019 | Yildirim et al. |
| 2019/0224016 | A1 | 7/2019 | Walker et al. |
| 2019/0388078 | A1 | 12/2019 | Otto et al. |
| 2020/0289050 | A1 | 9/2020 | Moctezuma De La Barrera et al. |
| 2020/0352555 | A1 | 11/2020 | Ebbitt |

FOREIGN PATENT DOCUMENTS

| | | | |
|---|---|---|---|
| EP | 3 251 589 | A1 | 12/2017 |
| GB | 2 455 182 | | 6/2009 |

OTHER PUBLICATIONS

U.S. Appl. No. 62/894,130, filed Aug. 30, 2019, MAKO Surgical Corp. et al.

U.S. Appl. No. 62/905,037, filed Sep. 24, 2019, MAKO Surgical Corp.

International Search Report and Written Opinion for International Application No. PCT/US2015/032973, mailed Sep. 24, 2015, 14 pages.

International Search Report and Written Opinion for International Application No. PCT/US2020/022386, mailed Jul. 3, 2020, 18 pages.

International Search Report and Written Opinion for International Application No. PCT/US2020/051743, mailed Dec. 17, 2020, 8 pages.

June Okamoto, et al; 35th Annual Int Conf of the IEE EMBS, Robotic Tensor Device for Optimal Soft Tissue Balance in TKA , published Jul. 2013, Osaka, Japan: https://ieeexplore.ieee.org/stamp/stamp.jsp?tp=&arnumber=6611092.

* cited by examiner

1

SYSTEM AND METHOD FOR LIGAMENT BALANCING USING ROBOTICALLY HELD DEVICE

CROSS-REFERENCE TO RELATED PATENT APPLICATIONS

This application is a continuation of U.S. patent application Ser. No. 17/257,186, filed on Dec. 30, 2020, which is a 371 national phase application of PCT/US2020/051743, filed on Sep. 21, 2020, which claims the benefit of and priority to U.S. Provisional Application No. 62/905,037, filed on Sep. 24, 2019, all of which are hereby incorporated by reference herein in their entireties.

BACKGROUND

The present disclosure relates generally to surgical systems for orthopedic surgeries, and more particularly to surgical systems for total knee arthroplasty procedures. Total knee arthroplasty, colloquially referred to as knee replacement, is widely used to treat knee osteoarthritis and other damage to a patient's knee joint by replacing portions of the knee anatomy with prosthetic components. In a total knee arthroplasty procedure ligaments of the knee and the surrounding area are also affected and must be manipulated appropriately so as to accommodate prosthetic components introduced during the procedure.

One possible tool for use in total knee arthroplasty procedure is a robotically-assisted surgical system. A robotically-assisted surgical system typically includes a robotic device that is used to prepare a patient's anatomy, such as by making bone cuts, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

In order to properly place, accommodate, and position various prosthetic components required for a total knee arthroplasty procedure to achieve a proper joint performance post-procedure, the joint must be "balanced." This can refer to a proper soft tissue balance and/or proper gap balance in the knee joint. To balance soft tissue, such as ligaments, the various ligaments of the knee may be adjusted and manipulated. For example, ligaments such as the lateral collateral ligament (LCL) and the medial collateral ligament (MCL) may require tightening or loosening in order to achieve proper ligament tension through a range of motion and ultimately, proper joint function after placement of one or more prosthetic components. The introduction of prosthetic components can also alter gaps that exist within the knee. Depending on the state of the anatomical knee joint, introducing prosthetic components can either increase or decrease gaps within the knee joint. As such, gaps as well as ligaments of the knee joint may need to be balanced to accommodate normal range of motion of the knee joint for the patient. Similar to the balancing of ligaments, the balancing of gaps within the knee can require measurement of various parameters.

Obtaining proper balance of the ligaments of the knee is critical to the function of the knee. Just as total arthroplasty procedures can vary by patient, so too can the necessary ligament balancing within the knee. Products are available to measure various parameters of ligaments of the knee. Some products include complex manual apparatuses lacking digital components and data collection. Such manual apparatuses can be conducive to user error and subsequently may result in imbalanced ligaments within the knee of a patient. Other products include sensors configured to be positioned within the knee joint, for example wedged between the tibia and the femur. Such products may include digital components, but are designed for single-use and can be prohibitively expensive for some patients or procedures. That is to say that a cost-effective, reusable instrument capable of providing digital measurements for patient specific ligament balancing is desirable.

SUMMARY

One embodiment is a device for ligament balancing. The device includes a mount at a first end of the device, a head portion at a second end of the device, the head portion including a substantially planar surface, a first paddle, and a second paddle, wherein the first and second paddle are rotatable about a first longitudinal axis and a second longitudinal axis, respectively, relative to the substantially planar surface, a stem extending from the head portion, and a shaft extending between the stem and the mount. The mount includes a coupling portion configured to couple the device to a robotic device such that movement of the device is controlled by the robotic device.

In some embodiments, the device is a mechanical device void of any sensors and electrical components.

In some embodiments, the shaft is rotatable about a central axis relative to the mount.

In some embodiments, the shaft is tapered such that a diameter of the shaft is greater at a proximal end coupled to the mount and is smaller at a distal end coupled to the stem.

In some embodiments, the stem includes a bend such that a connection point between the stem and the head is offset from a central axis of the shaft.

In some embodiments, the first paddle and the second paddle are coupled to the head portion at opposite lateral sides of the head portion.

In some embodiments, the device includes a first lateral recess and a second lateral recess which receive the first paddle and the second paddle, respectively.

In some embodiments, the substantially planar surface includes a texture on the surface.

In some embodiments, the device is a component of a system including a robotic device having an articulated arm, wherein the device is coupled to a distal end of the articulated arm.

One embodiment is a robotic surgery system including a robotic device having an articulated arm, a surgical tool coupled to a distal end of the articulated arm, a force system configured to provide a force to the surgical tool by the articulated arm, a controller configured to generate control signals for controlling the force system, and a processor in communication with the robotic device and configured to receive information from the force system to measure the force provided by the articulated arm to the surgical tool.

In some embodiments, the surgical tool is a ligament balancing device and wherein the controller is configured to measure the force provided by the articulated arm when the ligament balancing device is being used to assess the ligament forces in a joint.

In some embodiments, the ligament balancing device includes a mount at a first end of the device, a head portion at a second end of the device, the head portion having a substantially planar surface, a first paddle, and a second paddle, wherein the first and second paddle are rotatable about a first longitudinal axis and a second longitudinal axis, respectively, relative to the substantially planar surface, a stem extending from the head portion, and a shaft extending between the stem and the mount, wherein the mount includes a coupling portion configured to couple the device to the articulated arm.

In some embodiments, the ligament balancing device is a mechanical device void of any sensors and electrical components.

In some embodiments, the shaft is rotatable about a central axis relative to the mount, and wherein rotation of the shaft and the first and second paddle allows for maximizing bone contact of the device with a bone surface when the ligament balancing device is being used to assess the ligament forces in the joint In some embodiments, the system includes a tracking system having a detection device and a tracker coupled to each of a first bone and a second bone of the joint, a navigation system for receiving data from the tracking system to determine at least one of a position and an orientation of the first bone and the second bone, and a processor in communication with the navigation system and configured to determine a gap between the first bone and the second bone using the data from the tracking system.

In some embodiments, the processor is further configured to correlate the force measurements and the gap between the first bone and the second bone as the joint is moved through a range of motion to determine a stiffness transition point of ligaments of the joint.

One embodiment is a method of assessing ligament balance in a joint including coupling a ligament balancing device to an articulated arm of a robotic device, applying, by a force system of the robotic device, a force to a bone of the joint by the ligament balancing device, and determining, by a processor in communication with the robotic device, the force applied to the bone of the joint by the ligament balancing device to assess the forces applied by one or more ligaments of the joint.

In some embodiments, the method includes tracking at least one of a position and an orientation of a first and a second bone of a joint using a tracking system and using data acquired by the tracking system to determine a gap between the first and second bone of the joint.

In some embodiments, the method includes correlating the force measurements and the gap measurements to determine a stiffness transition point of the one or more ligaments of the joint.

In some embodiments, the method includes adjusting at least one of a position and an orientation of a prosthetic component positioned in the joint or performing a ligament release in order to achieve a desired joint balance.

4

Figure 4:
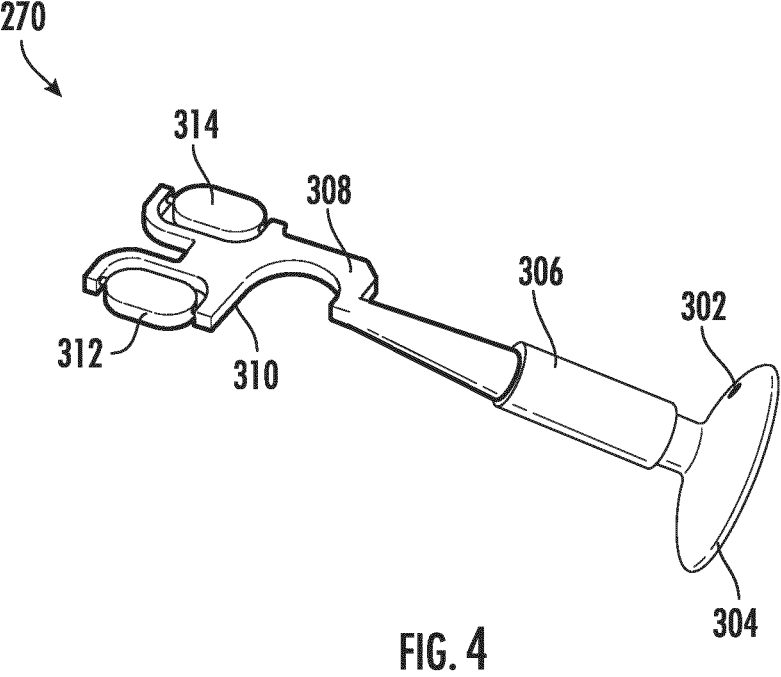

FIG. 4 is a perspective view of a ligament balancer for use in robotic and computer-assisted surgery, according to an exemplary embodiment.

Figure 5:
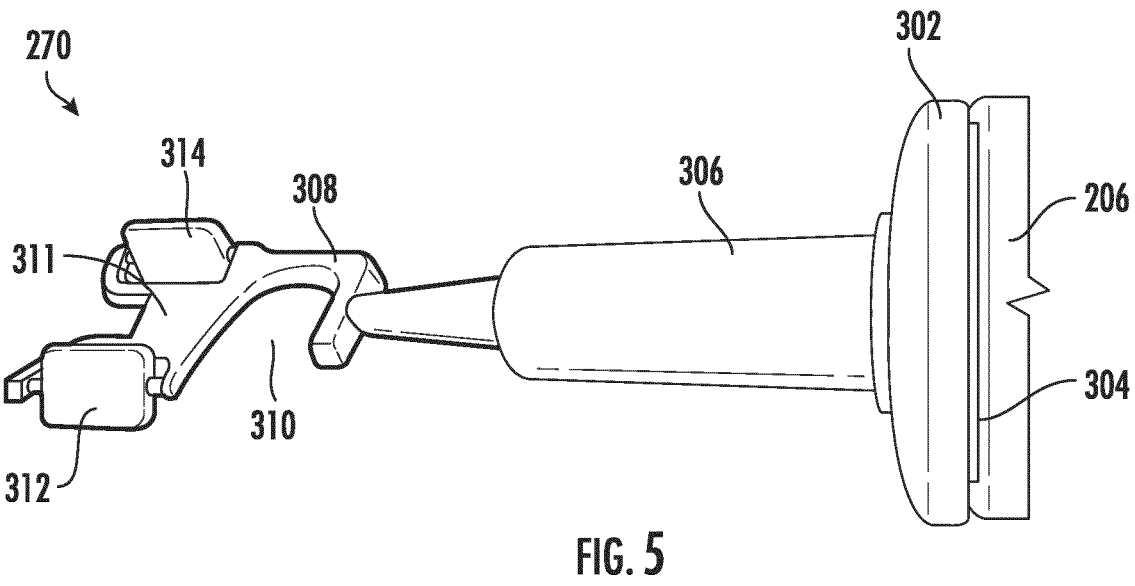

FIG. 5 is another perspective view of a ligament balancer for use in robotic and computer-assisted surgery, according to an exemplary embodiment.

Figure 6:
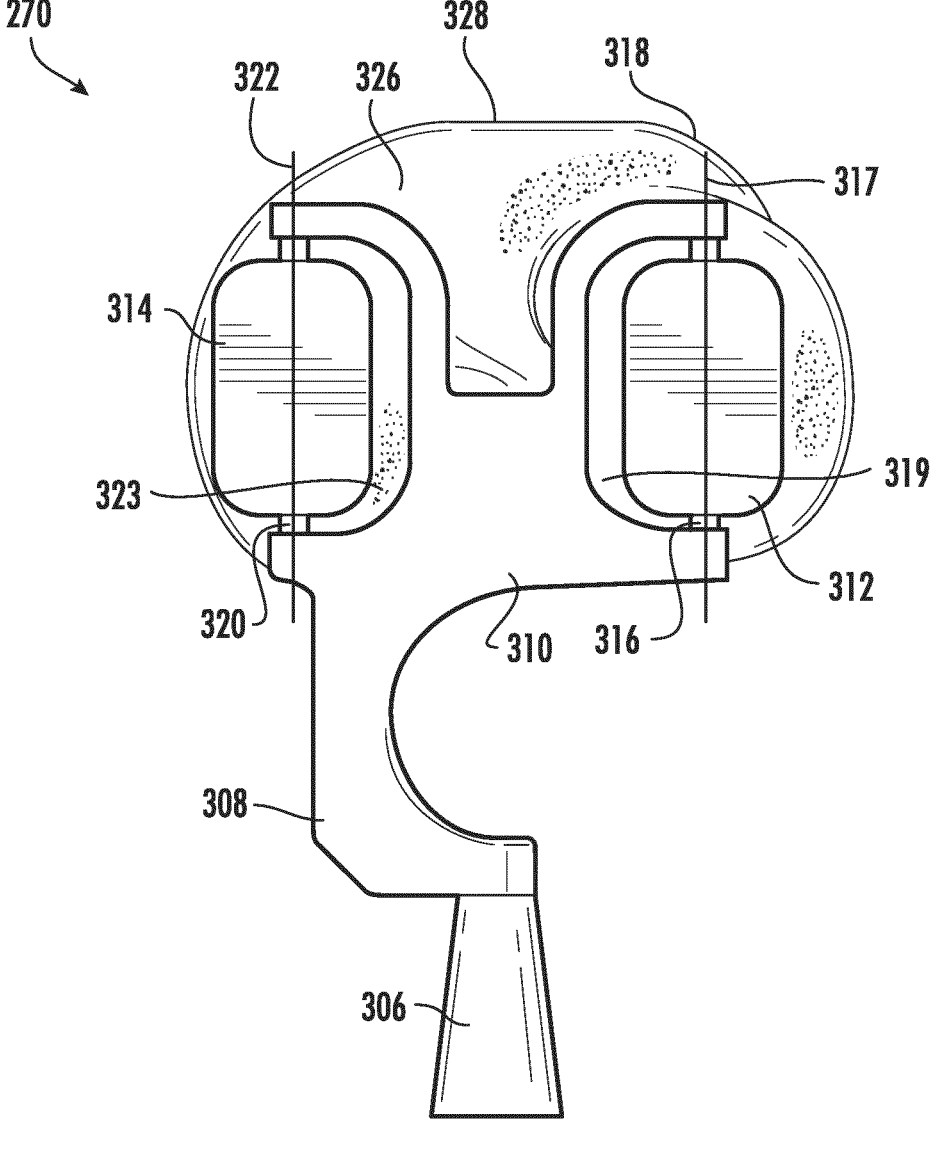

FIG. 6 is another perspective view of a ligament balancer for use in robotic and computer-assisted surgery, according to an exemplary embodiment.

Figure 7:
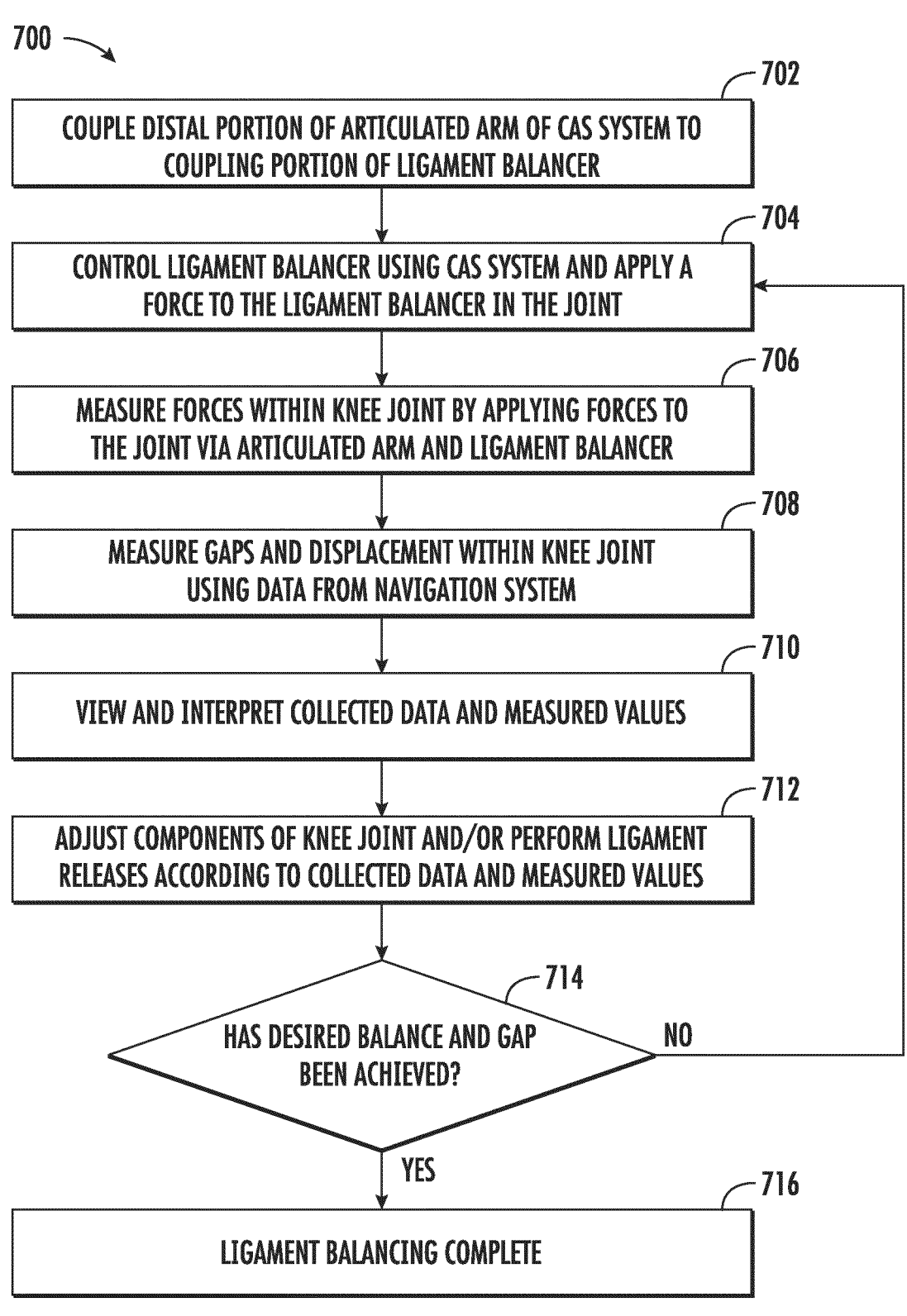

FIG. 7 is a flowchart of a process for implementing and operating a ligament balancer for use in robotic and computer-assisted surgery.

Figure 8A:
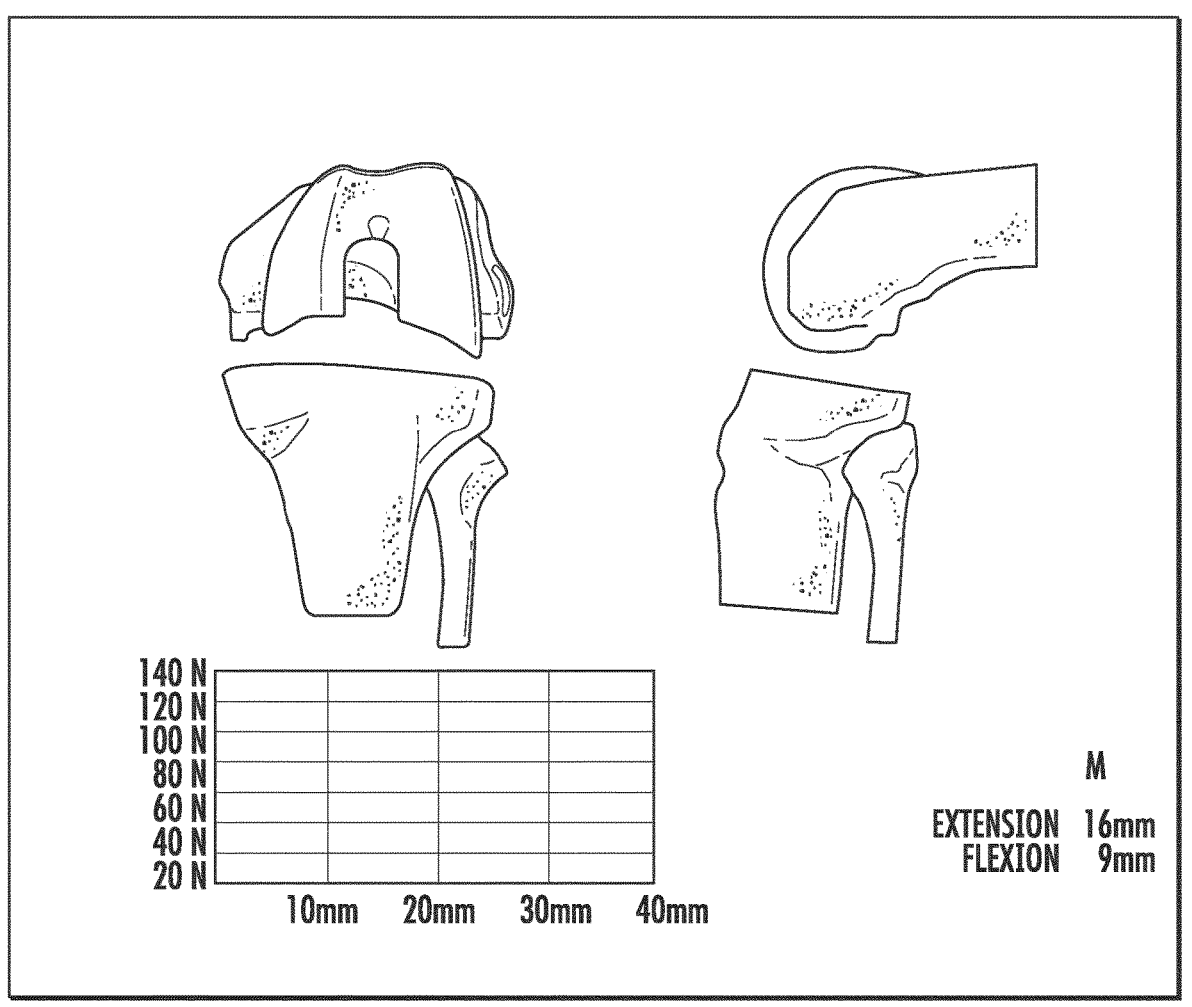

FIG. 8A is a plot that may be used to view data collected from use of a ligament balancer in robotic and computer-assisted surgery.

Figure 8B:
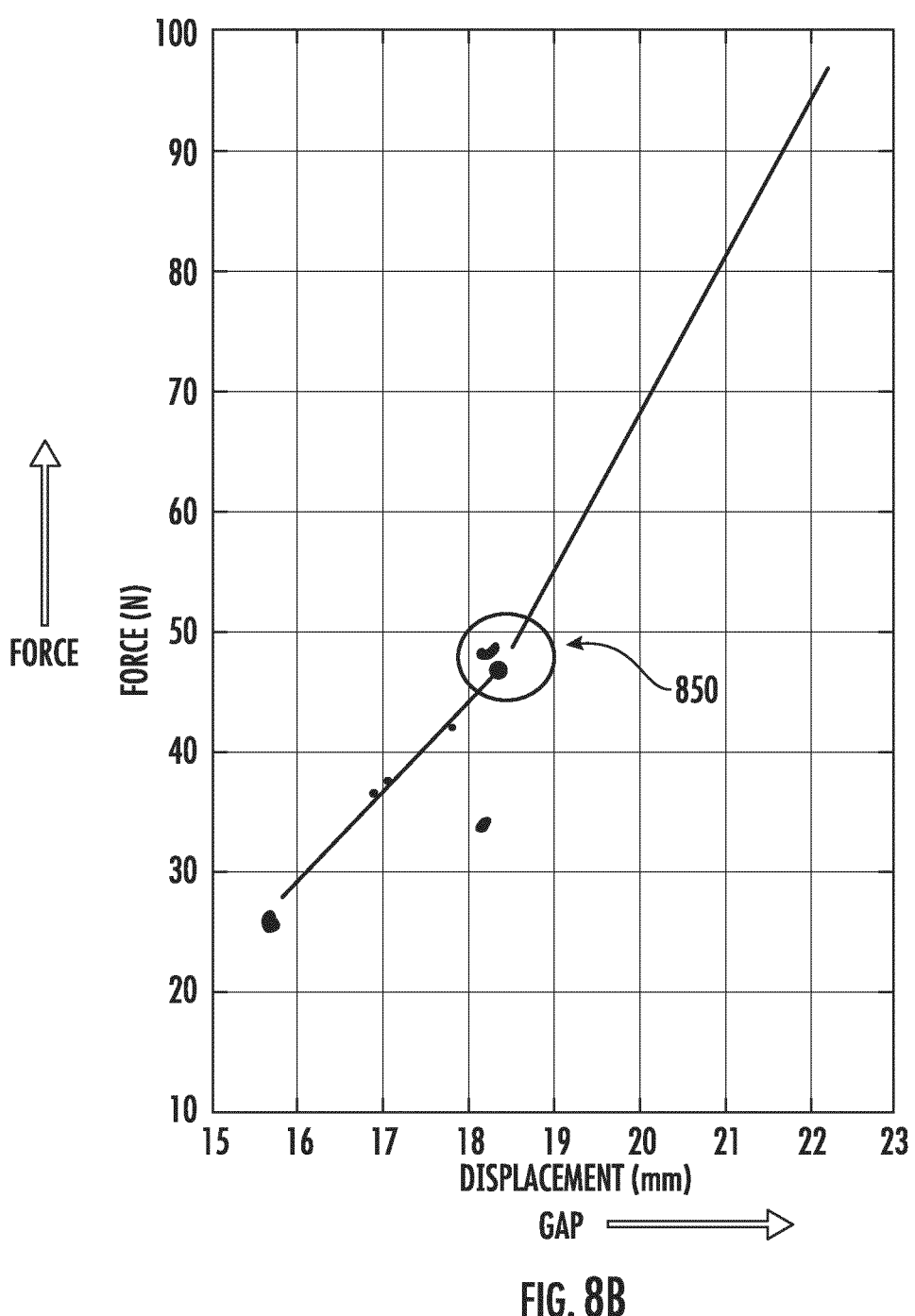

FIG. 8B is a plot showing data collected from use of a ligament balancer in robotic and computer-assisted surgery.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

It is important to note that the construction and arrangement of ligament balancer as shown in the various exemplary embodiments is illustrative only. Additionally, any element disclosed in one embodiment may be incorporated or utilized with any other embodiment disclosed herein. Furthermore, while the disclosure refers specifically to the knee joint, it is to be understood that the various exemplary embodiments may be modified and used for any joint which may require soft tissue and/or gap balancing.

Total knee arthroplasty, also known as total knee replacement, is a common procedure to address osteoarthritis of the knee as well as other possible damage to the knee joint (and, in some instances, surrounding tissue). Total knee arthroplasty procedures involve removing portions of the knee joint of the patient depending on specific ailment and replacing the removed portions of the knee joint with prosthetic components. Typically, total knee arthroplasty procedures involve modifying the distal portion of the femur and the proximal portion of the tibia to accommodate one or more prosthetic components. Robotically-assisted surgical systems, also known as computer-assisted surgery (CAS) are commonly used for some portions of total knee arthroplasty procedures such as, for example, making bone cuts.

In total knee arthroplasty procedures, various components of the knee are manipulated, repositioned, removed, and replaced. Commonly, the anterior cruciate ligament (ACL) and the posterior cruciate ligament (PCL) may be resected in order to facilitate the total knee arthroplasty procedure, while the lateral collateral ligament (LCL) and the medial collateral ligament (MCL) may be repositioned in order to accommodate prosthetic components introduced to the knee joint. Following a total knee arthroplasty procedure, the LCL and MCL are required to provide critical support of the knee joint but may require adjusting in order to function properly with newly introduced prosthetic components. In order to achieve ideal post-operative results, the ligaments require balancing. Failure to properly balance ligaments within the knee joint such as the LCL and the MCL may subject patients to valgus knees (bow-legged) or vagus knees (knock-kneed) which can be conducive to future knee problems and other health concerns. Additionally, gaps between various components within the knee can often be altered in a total knee arthroplasty procedure. For example, the introduction of additional components such as the prosthetic components installed in a total knee arthroplasty procedure may have slightly different anatomical features than the components they are replacing. Small variations in components of the knee joint can significantly alter critical gaps within the knee and subsequently impair movement between flexion and extension positions, for example. Measuring and adjusting gaps within the knee joint as well as balancing ligaments are critical to the success of a total knee arthroplasty procedure as well as the long-term health of the patient.

Figure 1:
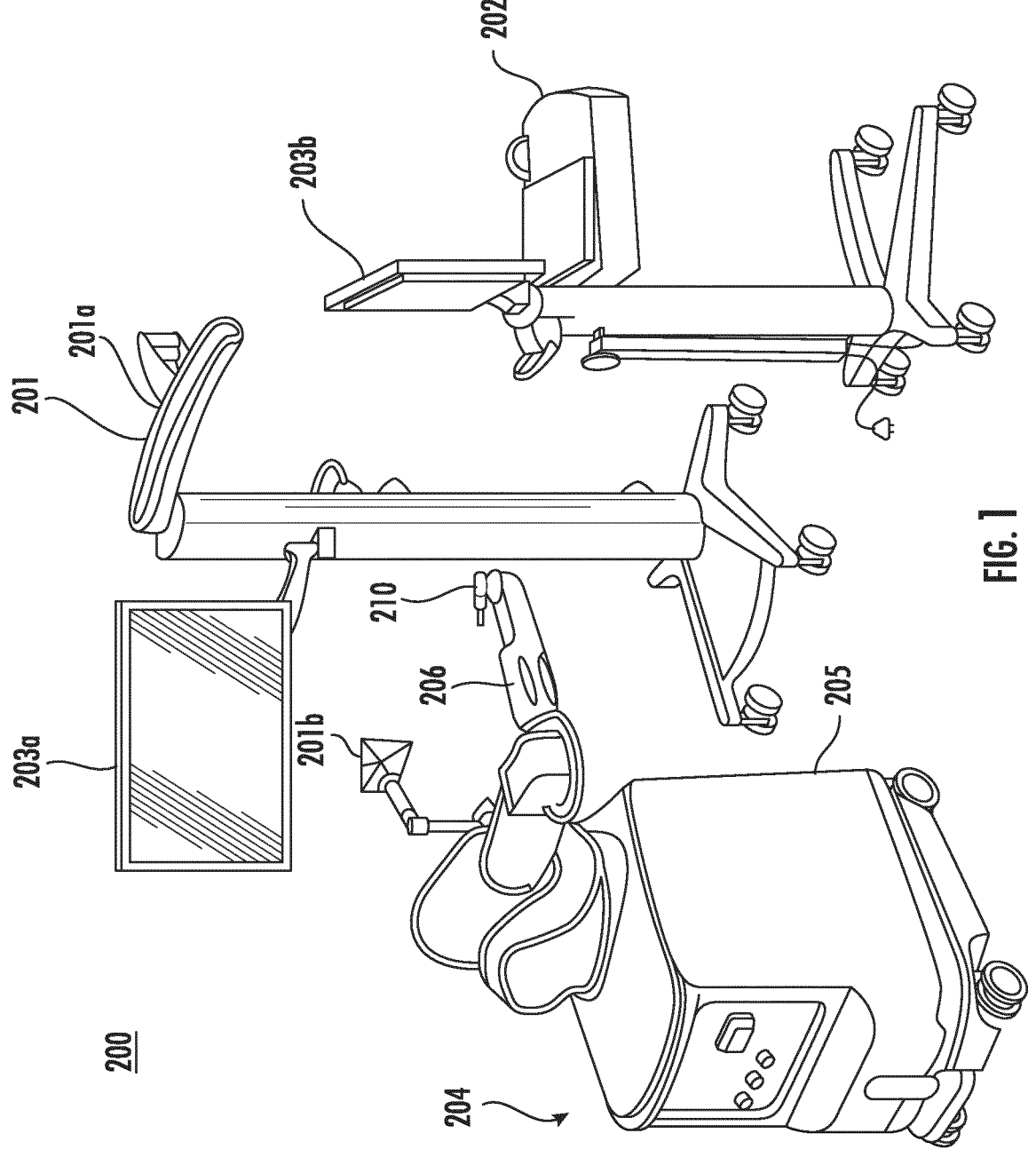
FIG. 1 is an illustration of a surgical system, according to an exemplary embodiment.

FIG. 1 illustrates an exemplary computer-assisted surgery (CAS) system 200, in which processes and features associated with certain disclosed embodiments may be implemented. CAS system 200 may be configured to perform a wide variety of surgical procedures, including total knee arthroplasty procedures. As illustrated in FIG. 1, CAS system 200 may comprise a tracking system 201, a computer-assisted navigation system 202, one or more display devices 203a, 203b, and a robotic device 204. It should be appreciated that CAS system 200, as well as the methods and processes described herein, may be applicable to many different types of surgical procedures. Although certain disclosed embodiments may be described with respect to drilling, resecting, and modifying portions of the knee joint and surrounding tissues during knee surgeries, those skilled in the art will appreciate that the concepts and methods described herein may be applicable to other types of surgeries. For example, concepts and methods described herein may be applicable to other procedures where portions of a patient's anatomy may be drilled, resected, or otherwise modified by CAS system 200.

Robotic device 204 can be used in an interactive manner by a surgeon to perform a surgical procedure, such as a total knee arthroplasty, on a patient. As shown in FIG. 1, robotic device 204 includes a base 205, an articulated arm 206, a force system (not shown), and a controller (not shown). Articulated arm 206 may include one or more joints about which articulated arm 206 may be pivoted, rotated, or otherwise moved. A surgical tool 210 (e.g., an end effector having an operating member, such as a saw, reamer, burr, drill, etc. or a measurement device) may be coupled to the articulated arm 206. The surgeon can manipulate surgical tool 210 by grasping and manually moving articulated arm 206 and/or surgical tool 210.

The force system and controller are configured to provide control or guidance to the surgeon during manipulation of the surgical tool. The force system is configured to provide at least some force to the surgical tool via articulated arm 206, and the controller is programmed to generate control signals for controlling the force system. In one embodiment, the force system includes actuators and a backdriveable transmission that provide force feedback to constrain or inhibit the surgeon from manually moving the surgical tool beyond predefined virtual boundaries defined by virtual objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. According to one embodiment, CAS system 200 is the RIO® Robotic Arm Interactive Orthopedic System manufactured by MAKO Surgical Corp. of Fort Lauderdale, Florida. The force system and controller may be housed within robotic device 204. Moreover, in certain embodiments, all or part of the force system may be housed within another component of CAS system 200, such as computer-assisted navigation system 202, for example.

Tracking system 201 may include any suitable device or system configured to track the relative locations, positions, orientations, and/or poses of the surgical tool 210 (coupled to robotic device 204) and/or positions of registered portions of a patient's anatomy, such as bones. Such devices may employ optical, mechanical, or electromagnetic pose tracking technologies. In some embodiments, a detection device 201a is used to determine the pose of one or more trackers 201b coupled to the surgical tool 210, portions of the patient's anatomy, or other components or devices used during the surgical procedure. Specifically, according to one embodiment, tracking system 201 may comprise a vision-based pose tracking technology, wherein an optical detector, such as a camera or infrared sensor, is configured to determine the position of one or more optical transponders. Based on the position of the optical transponders, tracking system 201 may capture the pose (i.e., the position and orientation) information of a portion of the patient's anatomy that is registered to that transponder or set of transponders.

Navigation system 202 may be communicatively coupled to tracking system 201 and may be configured to receive tracking data from tracking system 201. Based on the received tracking data, navigation system 202 may determine the position and orientation associated with one or more registered features of the surgical environment, such as surgical tool 210 or portions of the patient's anatomy. Navigation system 202 may also include surgical planning and surgical assistance software that may be used by a surgeon or surgical support staff during the surgical procedure. For example, during the surgical procedure, navigation system 202 may display images related to the surgical procedure on one or both of the display devices 203a, 203b.

Figure 2:
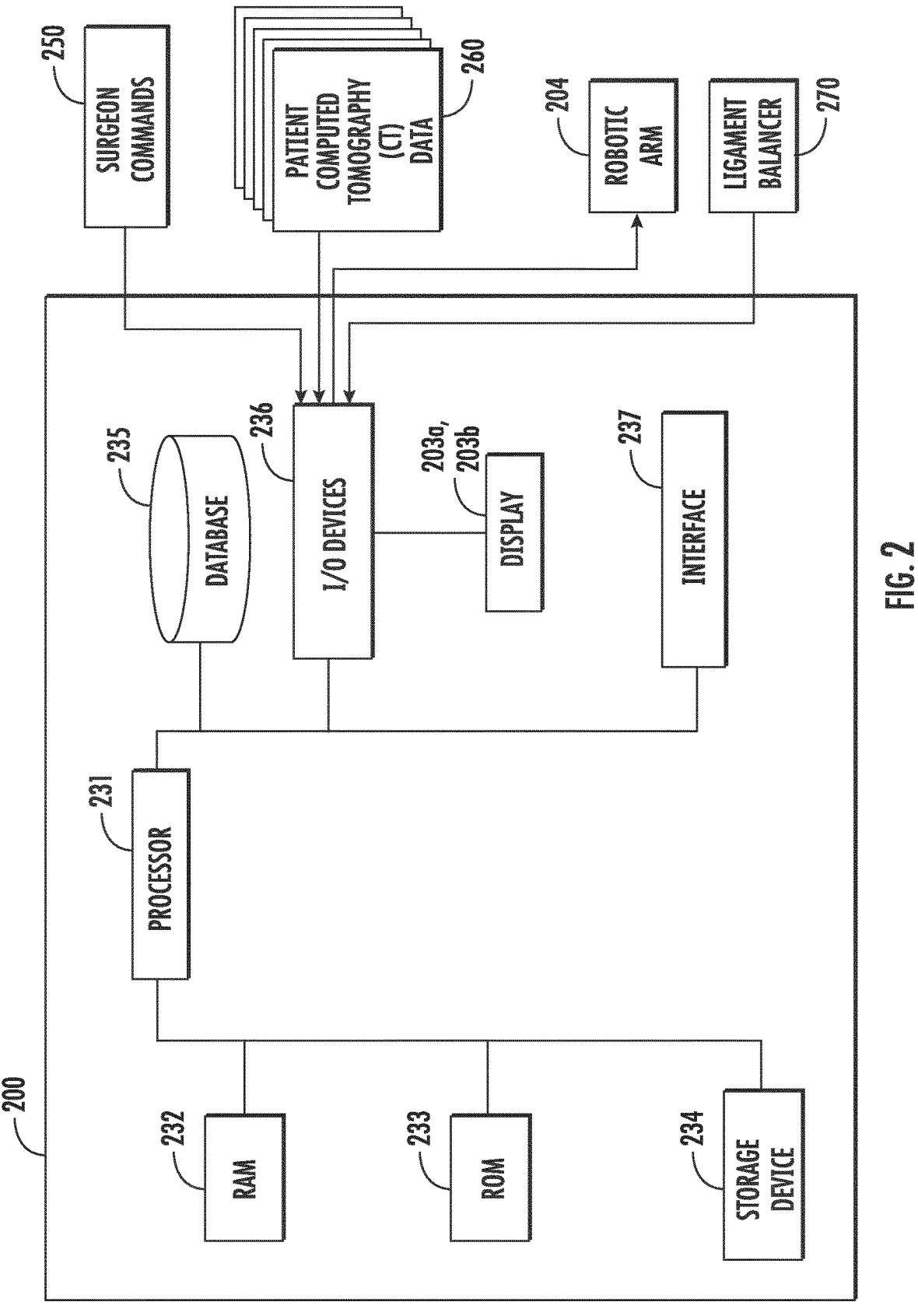
FIG. 2 is a diagram of system for computer-assisted surgery, according to an exemplary embodiment.

One or more constituent components of CAS system 200, such as navigation system 202 and/or robotic device 204, may include or embody a processor-based system (such as a general or special-purpose computer) in which processes and methods consistent with the disclosed embodiments may be implemented. For example, as illustrated in FIG. 2, CAS system 200 may include one or more hardware and/or software components configured to execute software programs, such as tracking software, surgical navigation software, 3-D bone modeling or imaging software, software for establishing virtual boundaries for use with the force system of robotic device 204 to provide force feedback to surgical tool 210, and/or software for providing dynamic feedback to a surgeon based on a measured distance between surgical tool 210 and a portion of the patient's anatomy, such as bones of the knee joint. In some embodiments, the virtual boundaries are virtual haptic boundaries and force feedback is provided by way of haptic feedback to the surgeon. CAS system 200 may include one or more hardware components such as, for example, a central processing unit (CPU) (processor 231); computer-readable media, such as a random access memory (RAM) module 232, a read-only memory (ROM) module 233, and a storage device 234; a database 235; one or more input/output (I/O) devices 236; and a network interface 237. The computer system associated with CAS system 200 may include additional, fewer, and/or different components than those listed above. It is understood that the components listed above are exemplary only and not intended to be limiting.

Processor 231 may include one or more microprocessors, each configured to execute instructions and process data to perform one or more functions associated with CAS system 200. As illustrated in FIG. 2, processor 231 may be communicatively coupled to RAM 232, ROM 233, storage device 234, database 235, I/O devices 236, and network interface 237. Processor 231 may be configured to execute sequences of computer program instructions to perform various processes, described in greater detail below. The computer program instructions may be loaded into RAM 232 for execution by processor 231.

Processor 231 may be configured to establish virtual geometries associated with or relative to one or more features of a patient's anatomy. As explained, CAS system 200 may be configured to create a virtual representation of a surgical site that includes, for example, virtual representations of a patient's anatomy, a surgical instrument to be used during a surgical procedure, a probe tool for registering other objects within the surgical site, and any other such object associated with a surgical site. During surgery, processor 231 may send haptic feedback commands to robotic device 204 based on the virtual geometry. For example, processor 231 may determine a distance between surgical tool 210 and one or more virtual representations, and may generate force feedback commands based on the distance. Processor 231 may also generate force feedback commands based on a measured distance between surgical tool 210 and a portion of a patient's anatomy.

Computer-readable media, such as RAM 232, ROM 233, and storage device 234, may be configured to store computer-readable instructions that, when executed by processor 231, may cause CAS system 200 or one or more constituent components, such as navigation system 202 and/or robotic device 204, to perform functions or tasks associated with CAS system 200. For example, computer readable media may include instructions for causing the CAS system 200 to perform one or more methods for dynamically altering a degree to which robotic device 204 (e.g., articulated arm 206) resists movement based on a relationship between a portion of the patient's anatomy and at least one of a position, an orientation, a velocity and an acceleration of a portion of the surgical tool 210. In certain embodiments, the instructions may cause CAS system 200 to alter the degree to which robotic device 204 resists movement by generating a damping torque based on the relationship between a portion of the anatomy and a portion of the surgical tool 210. In other embodiments, the instructions may cause CAS system 200 to alter the degree to which robotic device 204 resists movement by modifying an amount of force feedback being applied to robotic device 204 based on the relationship between a portion of the anatomy and a portion of the surgical tool 210. In still other embodiments, the instructions may cause CAS system 200 to alter the degree to which robotic device 204 resists movement by directly modifying a virtual object impedance value or virtual object admittance value based on the relationship between a portion of the anatomy and a portion of the surgical tool 210.

Computer-readable media may also contain instructions that cause tracking system 201 to capture positions of a plurality of anatomical landmarks associated with certain registered objects, such as surgical tool 210 or portions of a patient's anatomy, and cause navigation system 202 to generate virtual representations of the registered objects for display on I/O devices 236. Exemplary methods for which computer-readable media may contain instructions will be described in greater detail below. It is contemplated that each portion of a method described herein may have corresponding instructions stored in computer-readable media for causing one or more components of CAS system 200 to perform the method described.

I/O devices 236 may include one or more components configured to communicate information with a user associated with CAS system 200. For example, I/O devices 236 may include a console with an integrated keyboard and mouse to allow a user (e.g., a surgeon) to input parameters (e.g., surgeon commands 250) associated with CAS system 200. I/O devices 236 may also include a display, such as display devices 203a, 203b, including a graphical user interface (GUI) for outputting information on a monitor. I/O devices 236 may also include peripheral devices such as, for example, a printer for printing information associated with CAS system 200, a user-accessible disk drive (e.g., a USB port, a floppy, CD-ROM, or DVD-ROM drive, etc.) to allow a user to input data stored on a portable media device, a microphone, a speaker system, or any other suitable type of interface device. For example, I/O devices 236 may include an electronic interface that allows a user to input patient computed tomography (CT) data 260 into CAS system 200. This CT data may then be used to generate and manipulate virtual representations of portions of the patient's anatomy (e.g., bones) in software.

I/O devices 236 may also include one or more components configured to receive information about CAS system 200 and/or information related to a patient undergoing surgery. Moreover, other sensors (not shown) may also be included that measure, e.g., a position, velocity, and/or acceleration of surgical tool 210 and/or articulated arm 206 and send this information to processor 231.

I/O devices may also include a ligament balancer 270, described in greater detail below. Ligament balancer 270 may be coupled to robotic device 204 (e.g., to a distal end of articulated arm 206, as shown in FIG. 3B) and, in conjunction with robotic device 204, can aid in measuring force and gap within the knee, among other possible parameters. Ligament balancer may not include any digital components and may be a strictly mechanical instrument capable of functioning cooperatively with robotic device 204 as well as CAS system 200 and components thereof. Ligament balancer may aid the processor 231 in the collection of digital force readings, which may be stored in database 235, for example, and/or used by the surgeon completing the procedure for surgical planning.

Figure 3A:
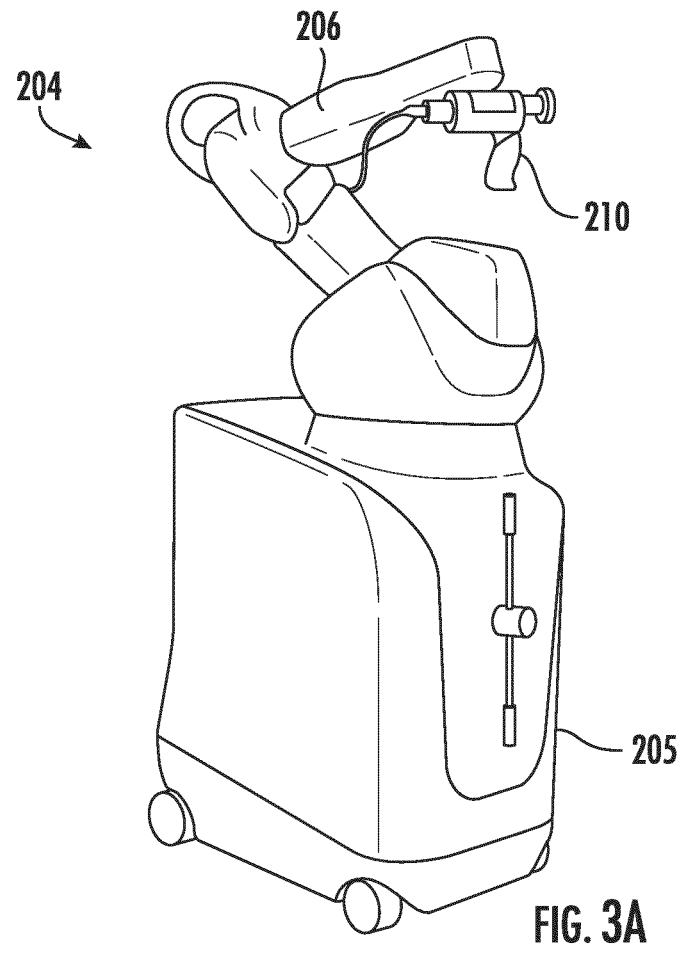
FIG. 3A shows a robotic device, according to an exemplary embodiment.
Figure 3B:
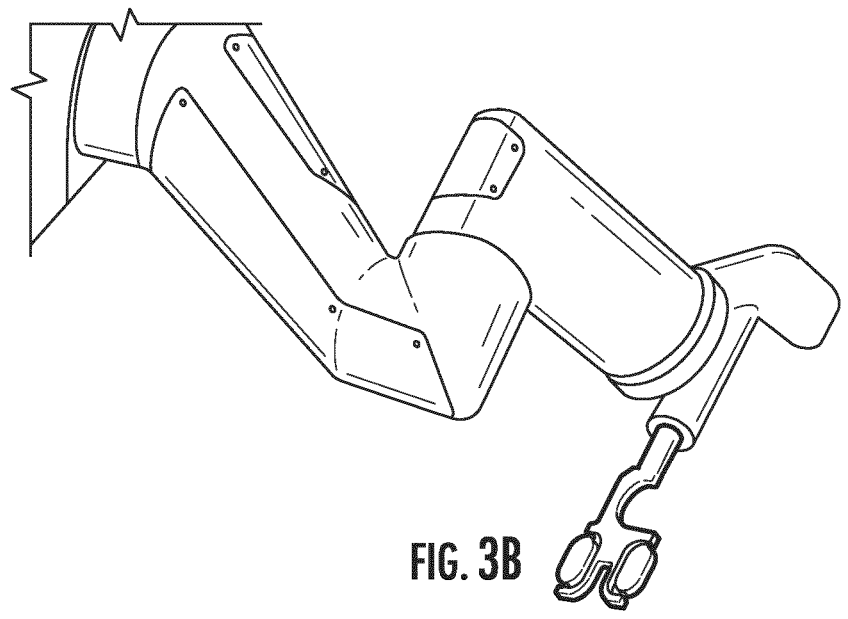
FIG. 3B shows the robotic device of FIG. 3A coupled to a ligament balancer, according to an exemplary embodiment.

Referring now to FIG. 3A, the robotic device 204 is shown. In some surgical procedures, such as total knee arthroplasty, robotic device 204 may be used to perform a number of functions. For example, a surgeon may use robotic device 204 to maximize cutting precision and planning accuracy for a given procedure. In a total knee arthroplasty, for example, robotic device 204 may perform cuts of the femur, as well as perform other surgical functions.

Robotic device 204 is shown to include base 205 and articulated arm. A surgical tool 210 is coupled to a distal end of articulated arm 206. In specific embodiments, the surgical tool 210 may be ligament balancer 270, as seen in FIG. 3B. Ligament balancer 270 can be manipulated using articulated arm 206.

Referring now to FIGS. 4-6, ligament balancer 270 is shown. Ligament balancer 270 is a mechanical component, configured to be comprised of one or more materials compatible with autoclaving procedures. In some embodiments, ligament balancer 270 is not a disposable component and may be used multiple times with multiple patients so long as properly sanitized. In other embodiments, however, ligament balancer 270 may be a disposable component configured to accommodate a single use. In surgical procedures such as total knee arthroplasty, ligament balancer 270 may be coupled to a distal portion of articulated arm 206 of robotic device 204 as seen in FIG. 3B.

Ligament balancer 270 is shown to include a mount 302, as well as a coupling portion 304. Mount 302 in configured to be circular, with coupling portion 304 configured on a side of mount 302. Coupling portion 304 is configured to be coupled to a component of CAS system 200, such as a distal end of the articulated arm 206 of robotic device 204, and manipulated during surgical procedures. Ligament balancer 270 is a mechanical component void of any sensors or digital components, which is to say that coupling between coupling portion 304 and articulated arm 206 is free from any wiring or other digital components. In a surgical environment in which blood and/or other bodily fluids may be present, limiting digital and/or electrical components may be desirable so as to prevent possible failure of digital or electrical systems due to the bodily fluids, and may be further desirable to protect patients from possible shock. Coupling mechanisms of articulated arm 206 and coupling portion 304 of ligament balancer 270 can vary according to different embodiments of both ligament balancer 270 as well as CAS system 200 and articulated arm 206. For example, complimentary recesses and protrusions of coupling portion 304 and/or articulated arm 206 may be configured to interface such that coupling is achieved.

Mount 302 of ligament balancer 270 is shown to include a shaft 306 extending from mount 302. As shown in the embodiments of FIGS. 4-6, shaft 306 is a tapered cylindrical component or has a tapered portion, such that a portion of the shaft 306 with the greatest diameter is at the proximal end of ligament balancer 270 (i.e. closest to the mount 302) and a portion of the shaft with the smallest diameter is toward the distal end of the ligament balancer. In some embodiments, the length and the taper of shaft 306 may vary so as to accommodate different surgical procedures and thereby allow ligament balancer 270 to be placed in various locations with a joint, such as a knee joint. Shaft 306 and mount 302 may further be coupled such that mount 302 is configured to maintain static coupling to articulated arm 206 via coupling portion 304, while allowing shaft 306 and other more distal portions of ligament balancer 270 to pivot relative to mount 302.

Ligament balancer 270 includes a stem 308 which extends from a distal portion of the shaft 306. As shown in FIGS. 4-6, stem 308 couples the shaft 306 to head portion 310 (described below) and includes a bend (for example, forms a L-shape) such that the location at which the stem 308 is coupled to the head portion 310 is offset from the central axis of shaft 306. Similar to shaft 306, stem 308 may be variable in different embodiments with parameters such as length and girth configured such that ligament balancer may be able to access specific portions of one or more joints, such as the medial-lateral gap of the knee in total knee arthroplasty procedures.

Ligament balancer 270 is shown to include a head portion 310, with head portion 310 extending from a distal portion of stem 308. In one embodiment, as shown in FIG. 5, head portion 310 includes a texture 311 on one or more surfaces thereof. In the exemplary embodiment of FIG. 5, texture 311 is shown to include a plurality of raised linear components. Texture 311 allows ligament balancer 270 to maintain contact with surface with which it interfaces, such as a portion of a prosthetic component or a bone of a patient in a total knee arthroplasty procedure. Head portion 310 is substantially planar and configured to confront a portion of a bone or prosthetic component in a joint. Head portion 310 is further shown to include a first paddle 312 and a second paddle 314. First paddle 312 and second paddle 314 are shown to be configured between the proximal portion and the distal portion of head portion 310, and are further configured laterally on opposite sides of head portion 310. Both first paddle 312 and second paddle 314 are configured to be pivotable, which is to say that they are each configured to swivel about a central axis running generally parallel to shaft 306.

As shown in FIG. 6, first paddle 312 is configured at an opposite side of head portion 310 from where stem 308 interfaces with head portion 310, and is further shown to include a first pin 316 running along a first longitudinal axis 318. First pin 316 is shown to extend through a first bore 317 of first paddle 312 along first longitudinal axis 318, with first pin 316 being coupled to head portion 310 at points on both the distal and proximal ends of first paddle 312 and subsequently coupling first paddle 312 to head portion 310. As such, first paddle 312 is configured to pivot about first longitudinal axis within a first lateral recess 319 of head portion 310, with first pin 316 being coupled to head portion 310 at points on both the proximal and distal sides of first lateral recess 319. Second paddle 314 is similarly coupled to head portion 310 via a second pin 320 configured along a second longitudinal axis 322 and further configured to extend through a second bore 321 in second paddle 314. Second pin 320 is coupled to both the distal and proximal portions of a second lateral recess 323, allowing second paddle 314 to pivot about second longitudinal axis 322.

CAS system 200 and/or robotic device 204 can be used to manipulate ligament balancer 270. For example, when coupled to articulated arm 206 of CAS system 200, ligament balancer 270 may be moved and positioned, either by CAS system 200 and/or a surgeon, within a joint such as a knee joint during a total knee arthroplasty procedure. CAS system 200 and/or robotic surgery apparatus may be configured such that various data may be collected from the use of ligament balancer 270 including measured gaps within the joint (using tracking data from tracking system 201 and navigation system 202) and forces present within the ligaments for the knee, for example a tension force in the LCL and MCL.

Ligament balancer 270 is shown to contact bone 326, as shown in the exemplary embodiment of FIG. 6. It should be noted that, depending on the procedure and the patient, bone 326 may be a patient's bone, synthetic bone material, or a portion of a prosthetic component. For example, in the instance of a total knee arthroplasty procedure bone 326 may be a distal surface of the patient's femur or a proximal surface of the patient's tibia. Further to the previous example, bone 326 may also be a surface of the patient's femur or tibia exposed after a surgical cut has been made, with said surface of tibia or femur configured to interface with one or more prosthetic components to be installed within the knee joint. In yet another example, a surgeon may place temporary implant trials or other removable components in and/or around the knee joint so as to simulate bone or soft tissue surfaces. Such implants may be inserted prior to balancing, and ligament balancer 270 contacts one or more of said implants.

In FIG. 6, head portion 310 of ligament balancer 270 is shown to be substantially centered laterally over bone 326. In addition to head portion 310, both first paddle 312 and second paddle 314 are configured to contact bone 326. As described above, ligament balancer 270 is configured such that mount 302 is coupled, via coupling portion 304, to articulated arm 206 of CAS system 200. In such a configuration, shaft 306 and components distal thereof to which shaft 306 is directly or indirectly coupled are configured to pivot about a central axis 328 of the ligament balancer 270, seen in FIG. 6. When contacting bone 326, head portion 310 of ligament balancer 270 may pivot about central axis 328 (with shaft 306 and stem 308 also pivoting about central axis 328) such that head portion 310 achieves a position in which it contacts a maximum surface area of the surface of bone 326. As bone 326 may not be a flat surface and may include rough portions, both first paddle 312 and second paddle 314 are configured to pivot about first longitudinal axis 318 and second longitudinal axis 322, respectively, to achieve positions in which both first paddle 312 and second paddle 314 contact a maximum surface area of bone 326. Ligament balancer 270 may also be manipulated by CAS system 200 and/or robotic device 204 such that robotic device 204 and articulated arm 206 reposition ligament balancer 270.

As head portion 310, first paddle 312 and second paddle 314 contact bone 326, various measurements can be taken by CAS system 200. In some embodiments, ligament balancer 270 is a purely mechanical device and does not incorporate any sensors or digital components. In such embodiments, ligament balancer 270 is not configured to directly collect data or take measurements. Instead, in such embodiments, ligament balancer 270 is coupled to the distal portion of articulated arm 206 and manipulated by CAS system 200 and/or robotic device 204, and ligament balancer 270 contacts bone 326 such that a force provided by articulated arm 206 is applied to bone 326. For example, in the instance of a total knee arthroplasty procedure, bone 326 may be the patient's femur, and is coupled to both the LCL and the MCL. Over the course of the procedure, the surgeon will likely elect to balance the LCL and the MCL, and may do so by implementing the robot with ligament balancer 270 coupled to the distal end of the articulated arm 206. Using CAS system 200, ligament balancer 270 may be positioned adjacent to bone 326 such that head portion 310, first paddle 312 and second paddle 314 contact bone 326. By then applying a force by the articulated arm 206 through the ligament balancer 270 to bone 326, CAS system 200 may measure forces present in the joint (i.e. the tightness of the ligaments) by determining the force applied by CAS system 200 via ligament balancer 270 to the bone 326. In other embodiments, ligament balancer 270 may be equipped with one or more sensors in order to directly collect data and/or take measurements independently from or in conjunction with CAS system 200. For example, head portion 310 may comprise one or more sensors coupled to one or both of the first paddle 312 and second paddle 314. Additionally, in certain embodiments other components of ligament balancer 270 may also comprise sensors, such as shaft 306 and stem 308. Data and measurements collected at such sensors may be transmitted to the CAS system and used in a similar fashion as the measurements of force applied by the articulated arm, as described elsewhere herein.

In addition, CAS system 200, using data from tracking system 201 and navigation system 202, may measure various gaps in both flexion and extension, such as the medial gap and the lateral gap, which are known to be critical parameters in total knee arthroplasty procedures. Given measurement data as to the gap between the distal portion of the femur/femoral implant and the tibia/tibial implant, for example, the surgeon may adjust, re-measure, and re-adjust various components of the knee joint to achieve desired gaps and produce the best result of the total knee arthroplasty procedure. This gap information can be used in conjunction with the force measurements received by use of the ligament balancer 270 to provide a greater assessment of the joint balance.

Referring now to FIG. 7, a process 700 for implementing a ligament balancer for use in robotic and computer-assisted surgery is shown, according to an exemplary embodiment. It should be noted that ligament balancer of process 700 may be the same as or similar to ligament balancer 270 shown in FIGS. 4-6, and robotic and computer-assisted surgery components may be the same as and/or similar to robotic device 204 of FIG. 3 and CAS system 200 of FIG. 1, respectively. Another component of process 700 include an articulated arm which may be similar to articulated arm 206 of FIG. 1. Additionally, it should be noted that the steps outlined in process 700 are intended to illustrate one possible method for use of a ligament balancer in a surgical procedure such as a total knee arthroplasty. However, it should also be understood that the steps of process 700 are subject to change due to specifics of a patient, surgeon preferences, as well as other variables.

Process 700 is shown to include coupling the distal portion of the articulated arm of the CAS system to the coupling portion of the ligament balancer, according to an exemplary embodiment (step 702). Coupling portion of ligament balancer referenced in step 702 may be the same as or similar to coupling portion 304 of ligament balancer 270 as shown in the exemplary embodiment of FIG. 5. Additionally, coupling portion of ligament balancer referenced in step 702 may be configured to fit on multiple articulated arms of multiple CAS systems and as such care must be taken to ensure a secure and safe fit. Coupling portion of the ligament balancer may couple to the articulated arm through a variety of means including but not limited to latches, screws, and other securing and coupling mechanisms.

Process 700 is further shown to include moving the ligament balancer into desired positions within the knee joint using the CAS system and the articulated arm, according to an exemplary embodiment (step 704). A surgeon may desire measurements of various parameters within the knee joint prior to the introduction of permanent prosthetic components in order to adjust components of the knee joint during the procedure to achieve the same or similar measured parameters after the introduction of permanent prosthetic components. Depending on the patient and the surgeon, the desired positions within the knee joint may vary to include positions to measure various forces and displacements in different areas of the knee joint. Step 704 may be performed before the knee joint is altered and before any permanent prosthetic components are introduced. Alternatively, the ligament balancer may be positioned in a non-native joint. For example, before positioning the ligament balancer 270, a surgeon may alter the bone, attach devices to simulate the native anatomy prior to disease, or insert components to simulate the final prosthetic to be inserted, or any combination thereof.

Process 700 is further shown to include measuring forces within the knee joint by applying forces to various surfaces via the articulated arm and the ligament balancer, according to an exemplary embodiment (step 706). In some procedures, step 706 may include the surgeon measuring forces within the knee joint, such as those of ligaments including the LCL and the MCL. One possible method of measuring ligament forces may include applying a known force to one or more surfaces within the knee joint, and then collecting data relative to the reaction of the joint and its components to the applied force. For example, a force may be applied to a distal portion of the femur/femoral implant in order to measure forces present in the LCL and the MCL. The forces may be measured by monitoring the current of joint motors within the robot arm, a load cell may be coupled to the robot arm that is configured to measure applied loads. Step 706 may be conducted multiple times, for example in various flexion and extension poses throughout the range of motion of the joint, to measure different forces that may be present within the knee and ultimately affect the balancing of the knee joint. Additionally, step 706 may include using the ligament balancer to hold a portion of the knee joint, such as a first bone, in a fixed position while a surgeon manipulates one or more other portions of the knee joint, such as the second bone. The ligament balancer 270 and/or the CAS system measures the forces applied by the surgeon during the manipulation. Furthermore, in step 706, forces applied by the ligament balancer 270 may also be measured.

Process 700 is further shown to include measuring gaps and displacement within the knee joint while manipulating the articulated arm and ligament balancer, according to an exemplary embodiment (step 708). A tracker 201*b* may be coupled to each bone of the joint, for example to the femur and to the tibia. During step 708, data from the tracking system 201 is provided to the navigation system 202 to characterize the position and orientation of the bones of the joint and thereby determine a gap between, for example, the distal end of the femur and the proximal end of the tibia (or components placed thereon) throughout a range of motion as a force is applied by the ligament balancer 270. In some embodiments, step 708 of process 700 is optional. The results of step 706 and 708 can be used together to identify the soft tissue characteristics, and particularly, a stiffness transition point, as described in more detail below.

The conclusion of the measurements performed in steps 706 and 708 (i.e., the balancing tests) may be defined by various parameters including a force limit or a load limit. Additionally, such limits may be surgeon-defined parameters or may be pre-programmed in the CAS system. Such pre-programmed parameters may be based on generic patient data, and may be adjustable. Patient attributes and anatomical factors such as mechanical axis, anatomical axis, and joint axis may influence and be taken into consideration when determining limits for the joint during testing.

Process 700 is further shown to include viewing and interpreting collected data and measured values, according to an exemplary embodiment (step 710). Upon collecting various data from the knee joint of the patient before and/or after introducing prosthetic components, the surgeon may elect to observe the collected data. In some embodiments, the CAS system may be configured to display the collected data in multiple formats, such as 3-dimensional visuals, graphs, numerical text, and/or graphics, on display device 203*a* and 203*b* or similar device. In some procedures or in research applications, various relationships between collected data may be analyzed so as to determine target values for the knee joint after the introduction of permanent prosthetic components. For example, for determining a stiffness transition point as described below. Additionally, collected data may be securely stored by a component such as database 235 of FIG. 2.

Process 700 is further shown to include adjusting components of the knee joint according to the collected data and measured values, according to an exemplary embodiment (step 712). Depending on measurements collected by the use of the ligament balancer and the CAS system, the surgeon may elect to adjust components of the knee joint so as to achieve target values. In some embodiments, adjustments may be made multiple times to multiple components so as to allow the knee joint to function properly and pass tests the surgeon may apply. In some embodiments, measurements collected in step 710 may confirm that the surgeon has configured any and all prosthetic components within the knee joint as desired in which case step 712 may be omitted.

Process 700 is further shown to include determining if the desired balance and gap has been achieved, according to an exemplary embodiment (step 714). Upon reviewing collected measured data and potentially adjusting components of the knee joint, a determination is made as to whether the performance and measurement of various parameters of the knee joint is deemed satisfactory. In the event that such a determination is made, the ligament balancing procedure is shown to be complete, with progression to step 716 (ligament balancing complete). In the event that the knee joint fails to perform satisfactorily, process 700 may have some or all steps repeated, likely beginning with step 704 in which the ligament balancer is manipulated using the CAS system into positions within the knee joint conducive to recording accurate measurements and collecting useful data.

Process 700 is further shown to include the completed ligament balancing process, according to an exemplary embodiment (step 706). It should be noted that process 700 may be repeated one or more times for the same components of the knee joint or for different components of the knee joint. It should also be noted that various steps of process 700 may be completed out of order or skipped according to patient specifics and surgeon preferences, as well as other factors.

Among the metrics that can be measured by CAS system 200 through the implementation of ligament balancer 270 are gap (displacement, typically in mm) and ligament balance (force, typically in N). CAS system 200 may measure metrics using previously mentioned methods such as applying forces to various surfaces within the knee, and manipulating ligament balancer 270 within the knee joint to locate various components of the joint and their respective displacement from each other. FIG. 8A shows two images of a knee joint, as well as a graph in the lower left-hand portion of the figure. The graph in the lower left-hand portion of FIG. 8A is shown to indicate measured force on the y-axis and measured gap on the x-axis. In some embodiments, as force is measured by ligament balancer 270 and gap determined by CAS system 200 using data from tracking system 201, CAS system 200 may generate a plot similar to that shown in the lower left-hand portion of FIG. 8A. For example, if the knee joint may have different gap displacements in different positions such as in flexion and extension. Additionally, different positions may also include different measured forces in one or more ligaments of the knee joint. As such, CAS system may plot collected data from the use of ligament balancer 270 as it is collected, allowing the surgeon to adjust CAS system 200 and/or components of the knee accordingly.

Similar to the plot shown in FIG. 8A, FIG. 8B shows a plot of measured force as a function of gap displacement as may be generated corresponding to use of ligament balancer 270 in a knee joint during a total knee arthroplasty procedure. The data shown in FIG. 8B is representative of force and displacement measurements collected from the manipulation of ligament balancer 270 using CAS system 200. For example, the graph shown as FIG. 8B indicated the force applied along central axis 328 of the ligament balancer 270. Additional calculations may also be performed in order to determine and display separate medial and lateral data and graphics. Other graphics may also be generated and displayed in addition to those shown in FIGS. 8A-B, such as charts indicating load, displacement, or rotation as well as 3-D plots of motion.

FIG. 8B is shown to include plotted data collected from the use of ligament balancer 270 for measured force (y-axis) as a function of gap displacement (x-axis), determined from data from the tracking system 201. As indicated by the data shown on the graph, as the force measured by the CAS system via the ligament balancer 270 increases, the gap displacement increases. A stiffness transition point 850 is identified on the plotted data. The stiffness transition point 850 represents the point where the ligament(s) of the joint transition from slackness to high stiffness. Specifically, it can be seen that at stiffness transition point 850, the gap displacement begins to increase more slowly, indicating that the ligament(s) are stiffer from that point on. Identification of the stiffness transition point 850 is possible, and is more accurate, by use of the ligament balancer in conjunction with the CAS system 200, and thereby allows for optimization of a surgical strategy and component placement for ideal post-operative results.

Prior to implementing ligament balancer 270 in practice with CAS system 200, CAS system 200 as well as robotic device 204 may be calibrated. One such method for calibration is through the use of a virtual spring process.

In some procedures, a surgeon may elect for implementation of ligament balancer 270 in conjunction with CAS system 200 prior to fitting the knee joint with prosthetic components. For example, prior to performing the total knee arthroplasty procedure, the surgeon may opt to take measurements such as displacement of various knee gaps as well as forces present within the knee to establish baseline values for a specific patient. Subsequently, after the total knee arthroplasty is complete the surgeon may then elect to again implement ligament balancer 270 in conjunction with CAS system 200 so as to balance ligaments such as the LCL and the MCL as well as align various gaps in different positions such as flexion and extension.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

What is claimed is:

1. A method of assessing ligament balance in a joint, comprising:

applying, by motors of joints of an articulated arm of a robotic device and via a ligament balancing device in contact with to a first bone of the joint, a force that holds the first bone in a fixed position while a second bone of the joint is manually manipulated and a force measurement is collected; and determining, by a processor in communication with the robotic device, a force applied to one or more ligaments of the joint based on the force measurement.

2. The method of claim 1, wherein the force is applied with a predetermined amount of force such that the force measurement varies with a second force applied to the second bone.

3. The method of claim 1, further comprising tracking a position of the first bone and a position of the second bone using a tracking system during the manual manipulation of the second bone to determine a gap between the first bone and the second bone of the joint.

4. The method of claim 3, further comprising correlating the force measurement and the gap to determine a tissue characteristic of the one or more ligaments of the joint, wherein the tissue characteristic is a stiffness transition point of the one or more ligaments of the joint.

5. The method of claim 1, comprising moving, by the articulated arm of the robotic device, the ligament balancing device to a plurality of different positions in the joint.

6. The method of claim 5, wherein the plurality of different positions in the joint correspond to displacing different areas of the joint.

7. The method of claim 3, further comprising providing an indication to adjust an orientation of a prosthetic component based on the gap to achieve a desired joint balance.

8. The method of claim 1, further comprising providing an indication to perform a ligament release to achieve a desired joint balance.

9. The method of claim 1, wherein the force measurement is collected using the motors of the joints of the articulated arm.

10. A device for ligament balancing, comprising:

an articulated arm having a ligament balancer coupled to a distal end of the articulated arm; and one or more processors configured to generate control signals for controlling the articulated arm and to receive information from the articulated arm, the one or more processors configured to perform operations comprising:

controlling the articulated arm to move the ligament balancer into a plurality of different positions in the joint, including into contact with a first bone of the joint such that the articulated arm applies a distraction force to the joint;

determining a magnitude of the distraction force based on the information from the articulated arm.

11. The device of claim 10, wherein the plurality of the different positions correspond to measuring forces in different areas of the joint.

12. The device of claim 10, wherein the operations further comprise tracking a position of the first bone and a position of the second bone determine a gap between the first bone and the second bone of the joint.

13. The device of claim 12, wherein the operations further comprise correlating the magnitude of the distraction force and the gap to determine a tissue characteristic of the one or more ligaments of the joint.

14. The device of claim 13, wherein the tissue characteristic is a stiffness transition point of the one or more ligaments of the joint.

15. The device of claim 12, wherein the operations further comprise providing an indication to adjust an orientation of a prosthetic component based on the gap to achieve a desired joint balance.

16. The device of claim 10, wherein the information comprises a force measurement collected using motors of joints of the articulated arm.

17. A robotic surgery system, comprising:

a robotic device comprising an articulated arm;

a surgical tool coupled to a distal end of the articulated arm and comprising:

a stem extending from the distal end of the articular arm; and a surface extending away from the stem in a same direction that the stem extends from the distal end of the articular arm, the surface configured to contact a bone of a joint;

a controller programmed to:

control the articulated arm to move the surgical tool within the joint to a plurality of positions in the joint; and obtain, from the robotic device, data indicative of different forces associated with the plurality of positions in the joint.

18. The robotic surgery system of claim 17, wherein the surface is a fixed distance from the distal end of the articulated arm.

19. The robotic surgery system of claim 17, wherein the plurality of positions correspond to displacement of different areas of the joint.

20. The robotic surgery system of claim 17, wherein the data indicative of the different forces are measurement collected by joints of the articulated arm.

* * * * *